(12) United States Patent
Keoshian et al.

(10) Patent No.: US 9,387,109 B2
(45) Date of Patent: Jul. 12, 2016

(54) CARPAL TUNNEL BRACE

(71) Applicants: Craig Keoshian, Valencia, CA (US);
Russell Moir, Solvang, CA (US)

(72) Inventors: Craig Keoshian, Valencia, CA (US);
Russell Moir, Solvang, CA (US)

(*) Notice: Subject to any disclaimer, the term of this patent is extended or adjusted under 35 U.S.C. 154(b) by 326 days.

(21) Appl. No.: 13/851,370

(22) Filed: Mar. 27, 2013

(65) Prior Publication Data

US 2014/0296760 A1 Oct. 2, 2014

(51) Int. Cl.
*A61F 13/00* (2006.01)
*A61F 5/01* (2006.01)

(52) U.S. Cl.
CPC .................................... *A61F 5/0118* (2013.01)

(58) Field of Classification Search
CPC ......... A61G 13/12; A61F 5/3761; A61F 5/50; A61F 5/013; A61F 5/0118; A61F 5/0585; A61F 13/14; A61F 5/0113; A61F 5/0123; A61F 5/0111; A41D 13/05; A41D 13/08
USPC ........... 602/20–22, 61, 64; 2/21, 16; 128/878, 128/879, 869; D24/190–191
See application file for complete search history.

(56) References Cited

U.S. PATENT DOCUMENTS

| | | | | |
|---|---|---|---|---|
| 57,283 | A * | 8/1866 | Brown | 30/123.5 |
| 1,082,542 | A * | 12/1913 | Manson | 223/101 |
| 2,538,889 | A * | 1/1951 | Swarin | 2/21 |
| 2,561,863 | A * | 7/1951 | Holm | 602/79 |
| 3,238,939 | A | 3/1966 | Stubbs | |
| 3,533,407 | A | 10/1970 | Smith | |
| 3,598,408 | A | 8/1971 | Klose | |
| 4,190,054 | A * | 2/1980 | Brennan | 607/112 |
| D255,602 | S | 6/1980 | Finnieston | |
| D255,603 | S | 6/1980 | Finnieston | |
| D259,955 | S * | 7/1981 | Helferich | D24/190 |
| 4,287,609 | A * | 9/1981 | Amadeo | 2/16 |
| D300,948 | S | 5/1989 | Harris et al. | |
| 5,129,391 | A * | 7/1992 | Brodsky et al. | 607/110 |
| 5,376,066 | A * | 12/1994 | Phillips et al. | 602/21 |
| 5,413,553 | A * | 5/1995 | Downes | 602/21 |
| 5,538,501 | A | 7/1996 | Caswell | |
| 5,769,803 | A | 6/1998 | Brossard | |
| 5,916,187 | A * | 6/1999 | Brill | 602/21 |
| 6,142,966 | A | 11/2000 | Hely | |
| 6,179,751 | B1 * | 1/2001 | Clears | 482/48 |
| 6,196,985 | B1 | 3/2001 | Slautterback | |
| 6,569,111 | B2 | 5/2003 | Herzberg | |
| D477,409 | S | 7/2003 | Mills et al. | |
| D620,058 | S | 7/2010 | Gaedke | |
| 7,753,867 | B2 * | 7/2010 | Sorg | 602/66 |
| D645,564 | S | 9/2011 | Hinds | |
| 2002/0062095 | A1 * | 5/2002 | Slautterback | 602/21 |
| 2005/0197610 | A1 * | 9/2005 | Bennett | 602/22 |
| 2006/0064050 | A1 | 3/2006 | Jackson | |
| 2006/0149180 | A1 | 7/2006 | Phelen | |
| 2007/0293797 | A1 | 12/2007 | Koby et al. | |
| 2011/0130694 | A1 * | 6/2011 | Livolsi et al. | 602/21 |

* cited by examiner

*Primary Examiner* — Kim Lewis
(74) *Attorney, Agent, or Firm* — Felix L. Fischer

(57) ABSTRACT

A brace for relief of Carpal Tunnel Syndrome employs a strap element having a thumb aperture proximate a first end and a slot adjacent a peripheral edge of the strap element to receive a fifth finger. The strap element extends from the thumb aperture to be received in a central portion across a dorsal portion of a hand. The strap element then extends around the ulnar border and across the palm of the hand past the radial border with a tail portion of the strap element overlapping the central portion. A fastener moiety is provided on the tail portion of the strap element and a mating moiety on an outer surface of the strap element to engages the fastener moiety. The strap element tensioned around the hand produces approximation of carpals and metacarpals in the hand.

8 Claims, 7 Drawing Sheets

CARPAL TUNNEL BRACE

BACKGROUND INFORMATION

1. Field

Embodiments of the disclosure relate generally to the field of anatomical support braces and more particularly to a brace for relieving Carpal Tunnel Syndrome which is received over the thumb and creates tension around the hand to provide carpal approximation through approximating (closing) the metacarpals to detension the flexor tendons of the wrist and fingers, shortening the transcarpal ligament and putting the transcarpal ligament on slack to make patent (open) the carpal tunnel.

2. Background

In a normal open position of the hand, the carpal tunnel extending through the wrist is in a partially constricted configuration. Carpal Tunnel Syndrome is typically symptomatic of a repetitive motion injury which results in irritation and inflammation or swelling of the flexor tendons of the wrist and fingers in the common tendenous sheath which may affect the median nerve and ulnar artery and ulnar vein causing pain. Current treatment for Carpal Tunnel Syndrome is to employ a brace to merely immobilize the hand and wrist in either the neutral position or in a hyper extended position rotating the hand dorsally from the normal relaxed position extending from the wrist. While immobilizing the hand and potentially avoiding pain induced through movement, these forms of braces do not provide physical alteration of the musculoskeletal structure to relief the underlying physical cause of the pain.

It is therefore desirable to provide a carpal tunnel brace for relief of Carpal Tunnel Syndrome by altering musculoskeletal position to relieve symptoms by making the carpal tunnel patent.

SUMMARY

Embodiments disclosed herein provide a brace for use on the human hand which incorporates a strap element having a thumb aperture proximate a first end and a slot adjacent a peripheral edge of the strap element to receive a fifth finger. The strap element extends from the thumb aperture to be received in a central portion across a dorsal portion of a hand. The strap element then extends around the ulnar border and across the palm of the hand past the radial border with a tail portion of the strap element overlapping the central portion. A fastener moiety is provided on the tail portion of the strap element and a mating moiety on an outer surface of the strap element to engage the fastener moiety. The strap element tensioned around the hand produces approximation of carpals and metacarpals in the hand.

In an additional embodiment, a cold pack accessory is provided having a body to be received against the palm. an accessory fastener moiety is present on an outer surface of the body and a mating accessory moiety is provided on an inner surface of the strap element.

The embodiments provide a method for treatment of Carpal Tunnel Syndrome by engaging a thumb through an aperture in a strap element of a brace. The strap element is then extended around a hand in tension to approximate carpals and metacarpals in the hand. The strap element is then overlapped and secured.

The features, functions, and advantages that have been discussed can be achieved independently in various embodiments of the present disclosure or may be combined in yet other embodiments further details of which can be seen with reference to the following description and drawings.

DETAILED DESCRIPTION

Figure 1:
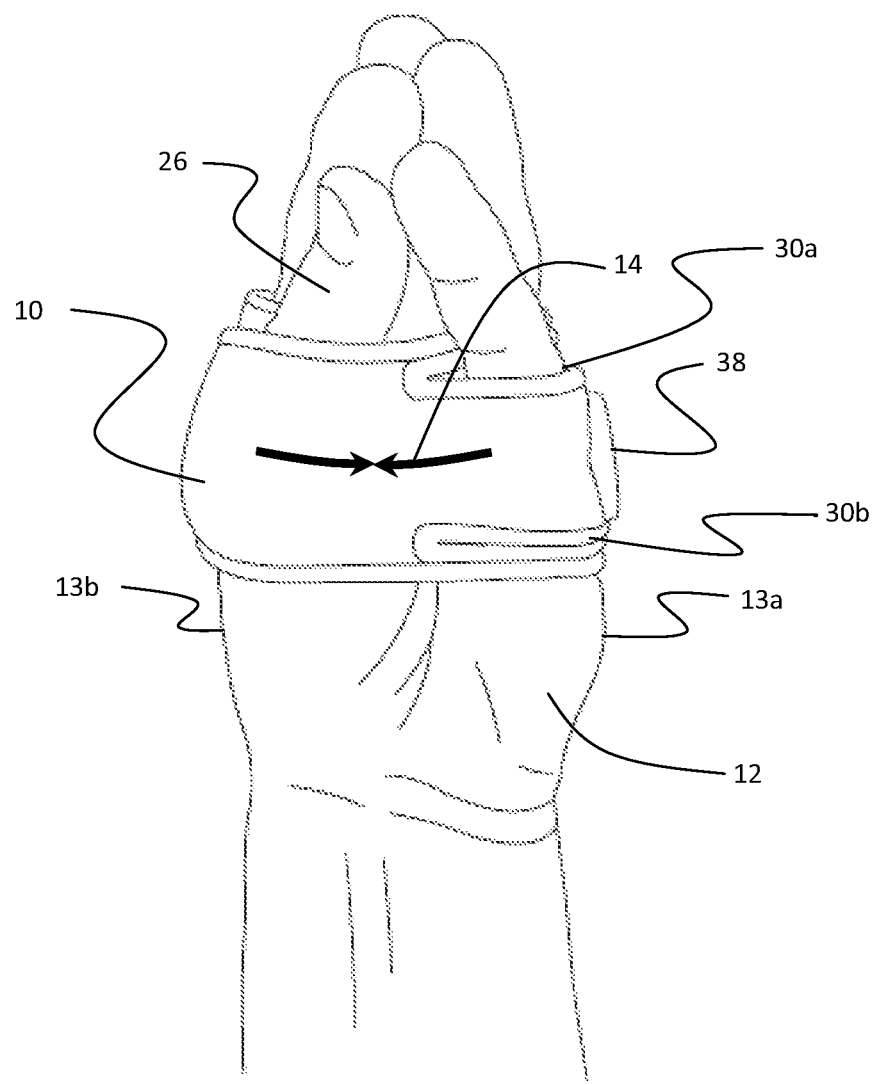
FIG. 1 is an illustration showing a hand with an embodiment of the present brace viewed from the ventral perspective.
Figure 2:
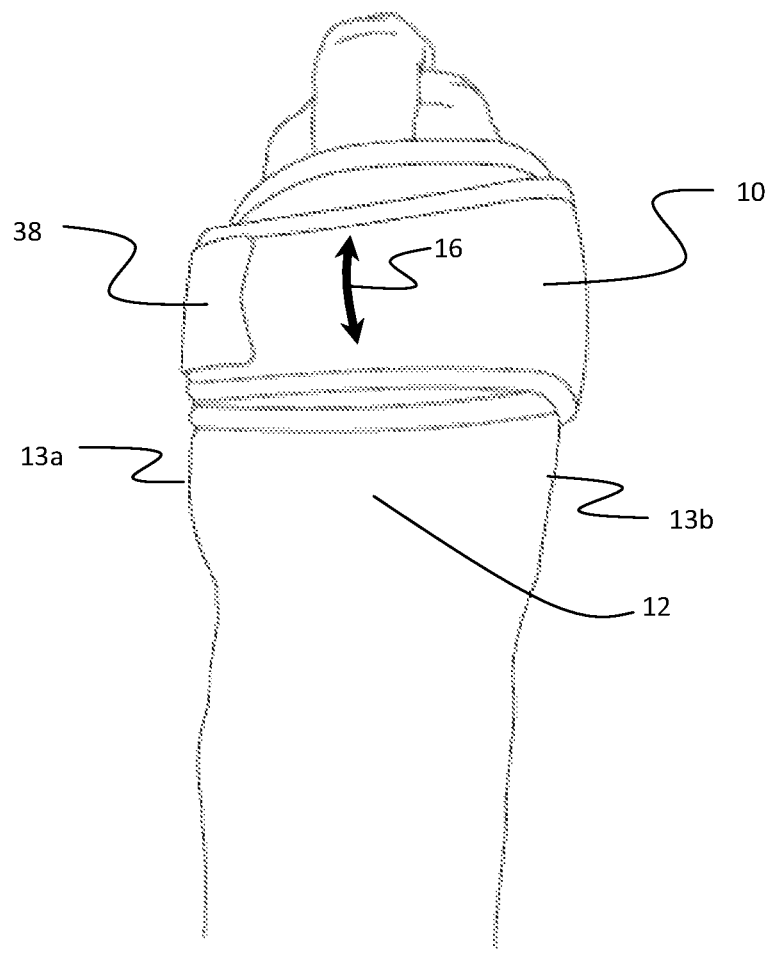
FIG. 2 is an illustration of the hand and brace of FIG. 1 viewed from a dorsal perspective.

Embodiments disclosed herein provide a brace 10 and treatment method which creates approximation (closing curvature) of the carpals and metacarpals in a hand 12 as shown in FIG. 1 with arrows 14. By approximating the metacarpals, the transcarpal ligament (TL) is shortened putting the TL on lax or slack. The flexor tendons of the wrist and fingers are also placed on slack. Tension in the Flexor Retiniculum (the muscle extending over the carpal tunnel from the thumb to $5^{th}$ finger) is also relaxed or slack in this position. Additionally, the brace urges the hand into an approximated position as indicated by the arrow 16 in FIG. 2. The combination of approximating the carpals and metacarpals results in making patent (opening) the carpal tunnel to allow maximum volume within the tendonous sheath for the flexor tendons, median nerve, ulnar artery and ulnar vein.

Figure 3A:
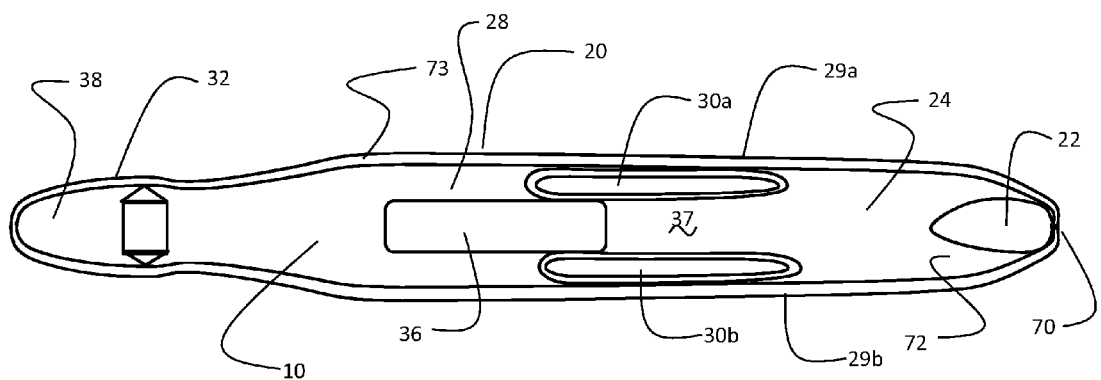
FIG. 3A is an outer view of a first embodiment of the brace.
Figure 3B:
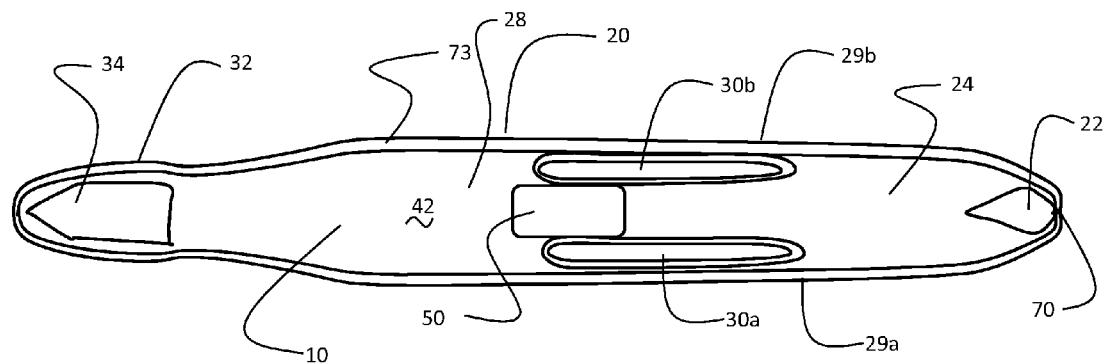
FIG. 3B is an inner view of the brace of FIG. 3A.

The brace 10 is show in detail in FIGS. 3A and 3B. A strap element 20 incorporates a thumb aperture 22 in a first end portion 24 through which the user's thumb 26 (shown in FIG. 1) is inserted. A central portion 28 of the strap element 20 is received over the outside or dorsal portion of the hand and includes slots 30a and 30b adjacent opposing peripheral edges 29a and 29b of the strap element 20 through one of which the fifth finger is received to act as a position fixation element as seen in FIG. 1. The opposing slots 30a and 30b on opposing edges of the strap element 20 allow ambidextrous universal fit for right or left handed application. A tail portion 32 of the strap element 20 provides a fastener moiety 34, employing a hook portion of a hook and loop fastener in the embodiments shown, on the bottom of the tail portion. The strap element and tail portion 32 wraps around an ulnar border 13a of the hand, across the palm or anterior portion of the hand past a radial border 13b, overlapping the first end portion extending from the user's thumb drawing the fifth finger metacarpophalangeal joint inward, (as seen in FIG. 1), and overlaps the central portion 28 of the strap. The fastener moiety 34 engages a mating moiety 36 on an outer surface 37 of the central portion 28, which may be a loop portion of the hook and loop fastener in the embodiment shown. The tail portion 32 may include a tab 38 which is more rigid than the strap element material for ease in connection and disconnection of the fastener moieties. In alternative embodiments the fastener moiety may be a snap head and mating fastener moiety may be a plurality of snap crowns arranged longitudinally along the back side of the central portion or one or more hooks with mating eyes arranged longitudinally along the back of the central portion for adjustable tension in the strap. In other embodiments, a D-ring may be mounted on the back of the central portion through which the tail portion is inserted and then drawn back in a reverse direction to fasten with the fastener moiety on the top side of the tail portion to engage the mating moiety on the central portion.

Upon fastening, the tension in the strap element 20 additionally pulls the thumb carpometacarpal basil joint inward toward the palm. In exemplary embodiments, the strap element 20 is fabricated from resilient fabric which allows stretching of the strap element slightly to increase and distribute the tension created on the closed strap. In the closed position the brace 10 approximates the carpals and metacarpals resulting in the desired making patent of the carpal tunnel.

Figure 4A:
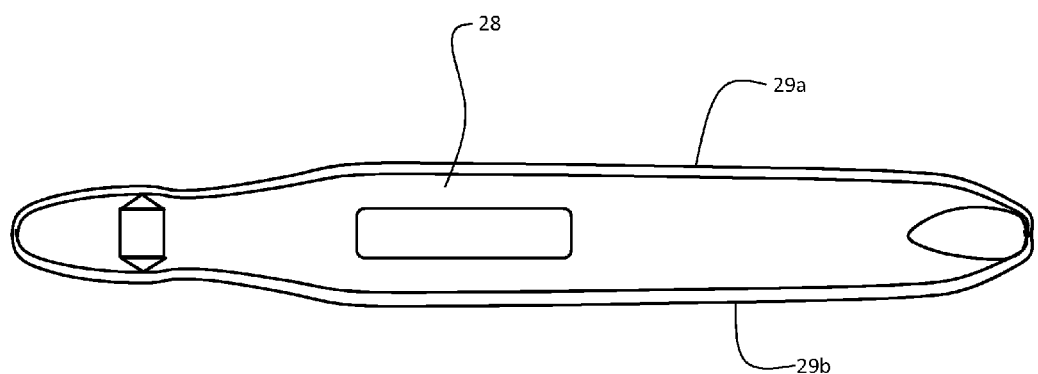
FIG. 4A is an outer view of a second embodiment of the brace.
Figure 4B:
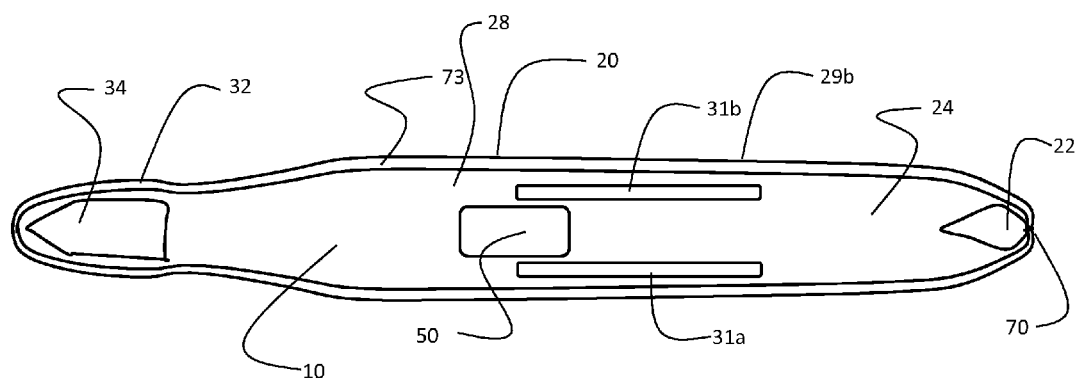
FIG. 4B is an inner view of the brace of FIG. 4A.

FIGS. 4A and 4B show a second embodiment of the brace with the slots 30a and 30b replaced by straps 31a and 31b engaged on the inner surface of the central portion 28 adjacent the peripheral edges 29a and 29b to act as the position fixation element. The fifth finger is inserted through one of the straps for fixing the position of the brace and opposing straps on opposite peripheral edges provides for the ambidextrous universal fit for right or left handed application.

Figure 5:
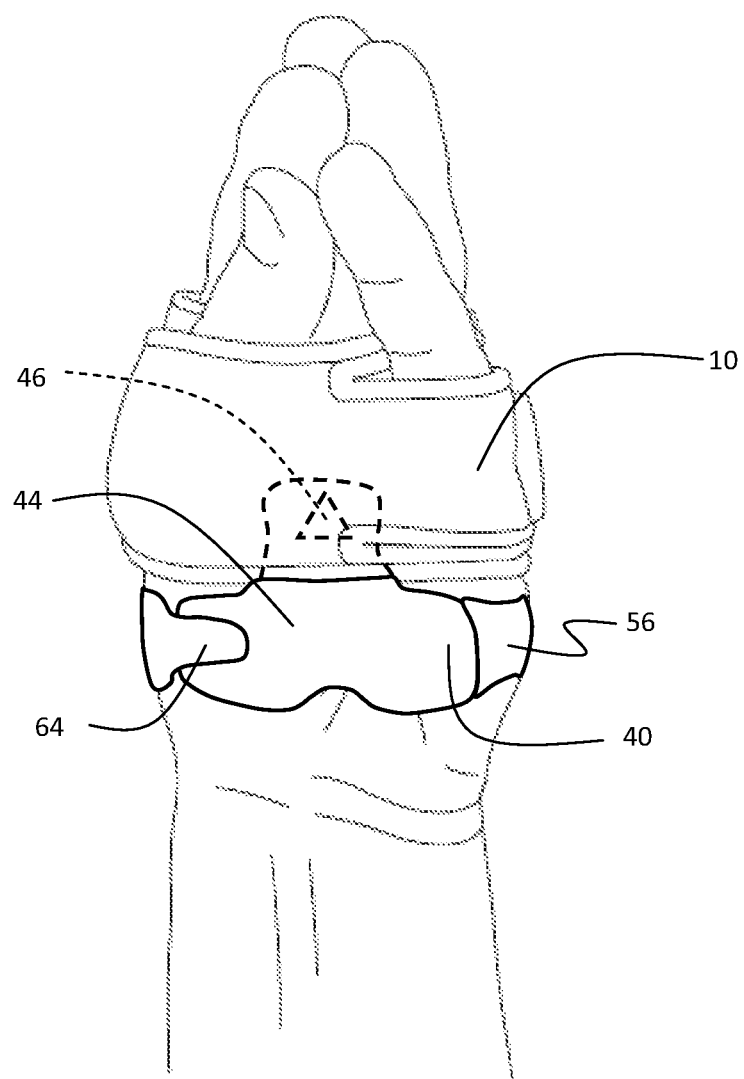
FIG. 5 is an illustration showing an additional cold pack accessory mounted to the brace to engage the palm of the hand.
Figure 6:
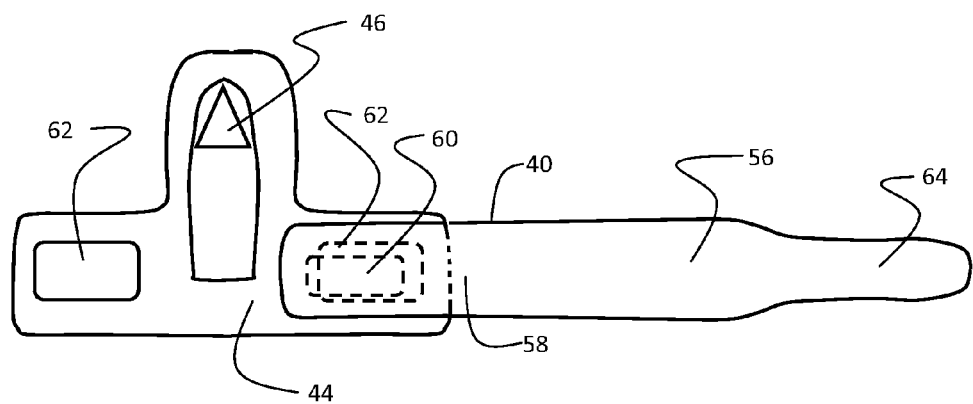
FIG. 6 is a outer view of the cold pack accessory.
Figure 7:
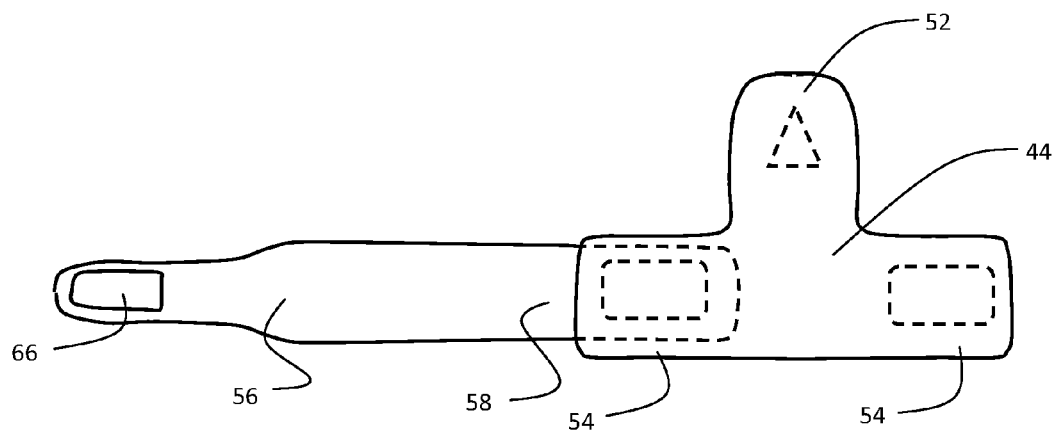
FIG. 7 is an inner view of the cold pack accessory.

To enhance the therapeutic capability of the brace 10, a cold pack accessory 40 is either integrally or removably attached. As shown in FIG. 5, the cold pack accessory 40 is engaged on the inside surface 42 of the central portion 28 of the strap element 20 (seen in FIG. 3B) to rest against the palm of the user's hand. The cold pack accessory 40 has a body 44 as shown in FIGS. 6 and 7 which includes a flexible water or gel packet. An accessory fastener moiety 46 is present on an outer surface 48 of the body 44 engages a mating accessory moiety 50 on the inside surface 42 of the strap element 20. For the embodiments shown, the accessory fastener moiety and mating accessory moiety are hook and loop fasteners with the hook portion as the accessory fastener moiety to avoid irritation of the user's palm by the mating accessory moiety if the cold pack accessory is not attached.

The body 44 is shaped in an inverted "T" for the embodiment shown to provide a central spine 52 to be received in the cupped center of the palm and extending arms 54 to engage the thenar and hypothenar of the palm. Width of the mating accessory moiety 50 allows lateral adjustment of the body 44 to match the hand size of the user. Precooling of the water or gel pack allows direct application of cold therapy to the palm with the cold pack accessory attached to the brace.

For additional security, the cold pack accessory 40 for the embodiment shown in the drawings employs a securing strap 56 attached at a first end 58 to one of the arms 54. In certain embodiments, the strap may be attached with a hook and loop or similar fastener 60 to be removable and a mating moiety 62 for the strap fastener may be provided on the outer surface of each of the arms 54 for ambidextrous positioning of the strap. A terminal end 64 of the strap includes a strap fastener moiety 66 to be engaged by the mating moiety 62 on the opposing arm 54 with the strap wrapped around the user's wrist as shown in FIG. 5.

Figure 3C:
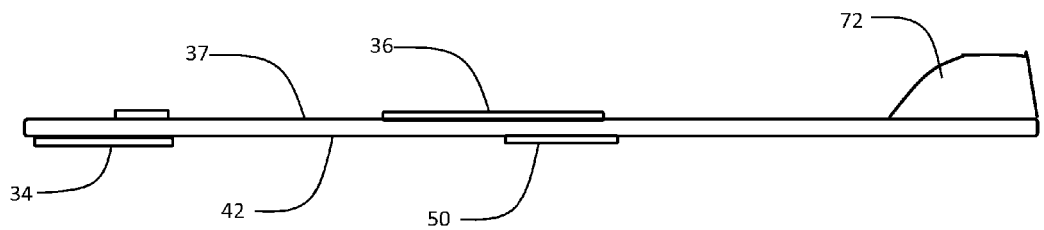
FIG. 3C is side view of the brace of FIG. 3A.

For an exemplary embodiment of the carpal tunnel brace, the strap element 20 is approximately 13¾ inches in length with the slots 30a and 30b approximately 3½ inches in from an initial end 70 (seen in FIGS. 3A and 4A) and 3 inches in length. Both the inner and outer surfaces of the may be covered with a "velvet" material to act as the loop portion of the mating fastener moiety 36 and the accessory mating fastener moiety 50. The strap element 20 may be produced from neoprene or similar resilient fabric and may be formed to provide a crown 72 (seen in FIG. 3C) surrounding the thumb aperture to provide smooth contouring of the brace when applied to the hand. Piping or ribbing 73 may be provided around the periphery of the brace, aperture and/or the slots to enhance structural integrity of the brace.

Figure 8:
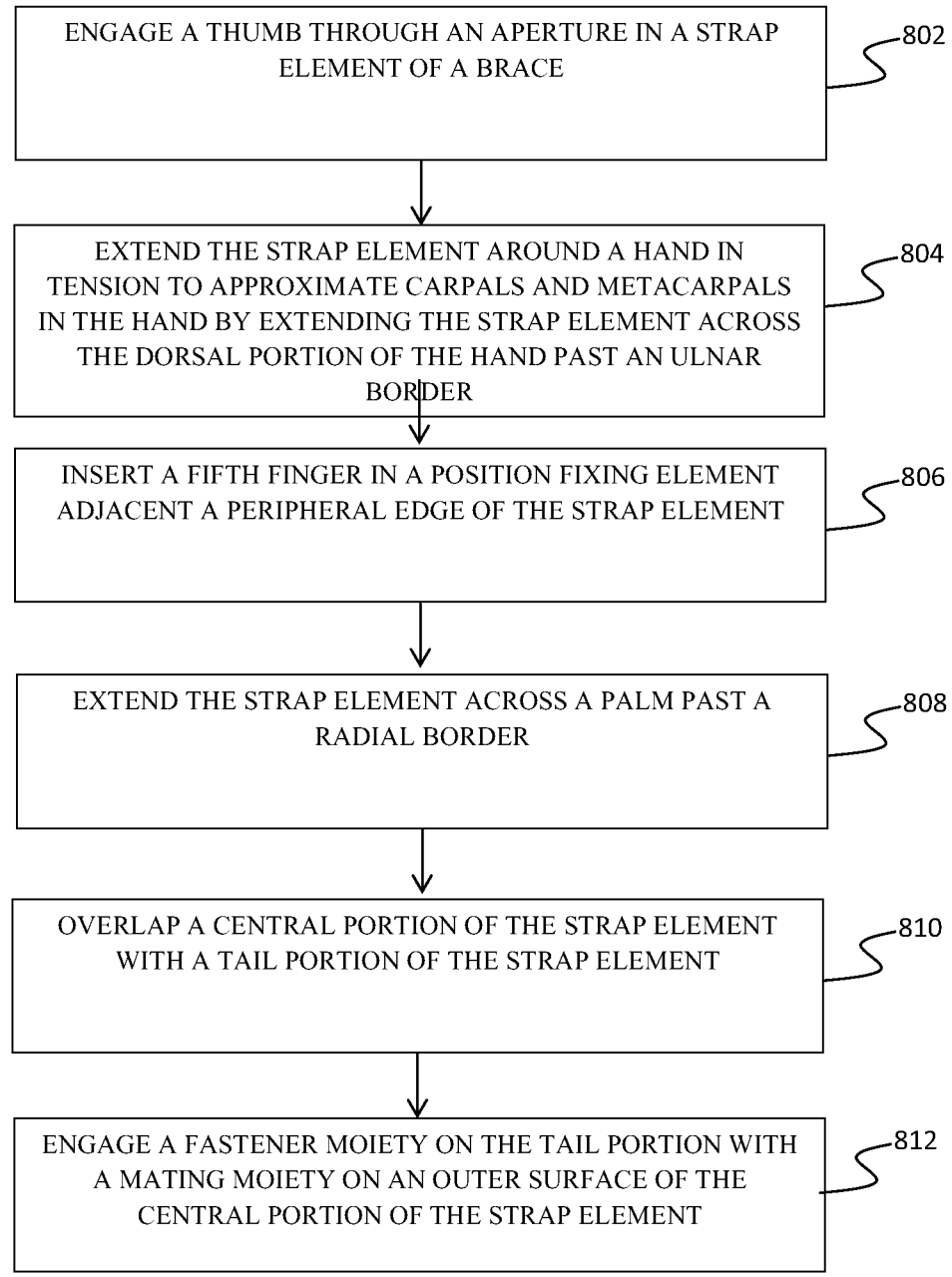
FIG. 8 is a flow chart of a method for employing the embodiments for relief of Carpal Tunnel Syndrome.

As shown in FIG. 8, the embodiments disclosed provide a method for treatment of Carpal Tunnel Syndrome by engaging a thumb through an aperture in a strap element of a brace, step 802. The strap element is extended around a hand in tension to approximate carpals and metacarpals in the hand by extending the strap element across the dorsal portion of the hand past an ulnar border, step 804, inserting a fifth finger in a position fixing element adjacent a peripheral edge of the strap element, step 806, then extending the strap element across a palm past a radial border, step 808. Overlap a central portion of the strap element with a tail portion of the strap element, step 810. A fastener moiety on the tail portion is engaged with a mating moiety on an outer surface of the central portion of the strap element, step 812.

Having now described various embodiments of the disclosure in detail as required by the patent statutes, those skilled in the art will recognize modifications and substitutions to the specific embodiments disclosed herein. Such modifications are within the scope and intent of the present disclosure as defined in the following claims.

What is claimed is:

1. A brace for use on the human hand comprising:
   a strap element having a thumb aperture proximate a first end and a first slot adjacent a peripheral edge of the strap element to receive a fifth finger, the strap element extending from the thumb aperture to be received in a central portion across a dorsal portion of a hand and adapted to extend around an ulnar border and across a palm of the hand past a radial border with a tail portion of the strap element overlapping the central portion wherein the strap element further incorporates a second slot adjacent an opposite peripheral edge of the strap for ambidextrous use of the brace;
   a fastener moiety on the tail portion of the strap element;
   a mating moiety on an outer surface of the strap element to engage the fastener moiety, said strap element adapted to be tensioned around the hand to produce approximation of carpals and metacarpals in the hand.

2. The brace as defined in claim 1 wherein the fastener moiety comprises a hook moiety and the mating moiety comprises a loop moiety.

3. The brace as defined in claim 1 wherein the strap element is fabricated from neoprene.

4. The brace as defined in claim 1 further comprising:
   a cold pack accessory having
      a body to be received against the palm, and,
      an accessory fastener moiety on an outer surface of the body; and,
   a mating accessory moiety on an inner surface of the strap element.

5. The brace as defined in claim 4 wherein the accessory fastener moiety and mating accessory moiety are a hook and loop fastener.

6. The brace as defined in claim 4 wherein the cold pack accessory further comprises:
   a securing strap attached to the body;
   a strap fastener moiety on an inner surface of the securing strap; and,
   a strap mating moiety on an outer surface of the body.

7. The brace as defined in claim 4 wherein the body is an inverted "T" shape having a central spine to be received against the palm and extending arms to engage a thenar and hypothenar of the palm.

8. The brace as defined in claim 4 wherein the body is an inverted "T" shape having a central spine to be received against the palm and extending arms to engage a thenar and hypothenar of the palm and further comprising:
   a securing strap attached to the body with a securing fastener moiety;
   a strap fastener moiety on a terminal end of the securing strap; and,
   a strap mating moiety on an outer surface of each arm of the body.

\* \* \* \* \*